Figure 1:
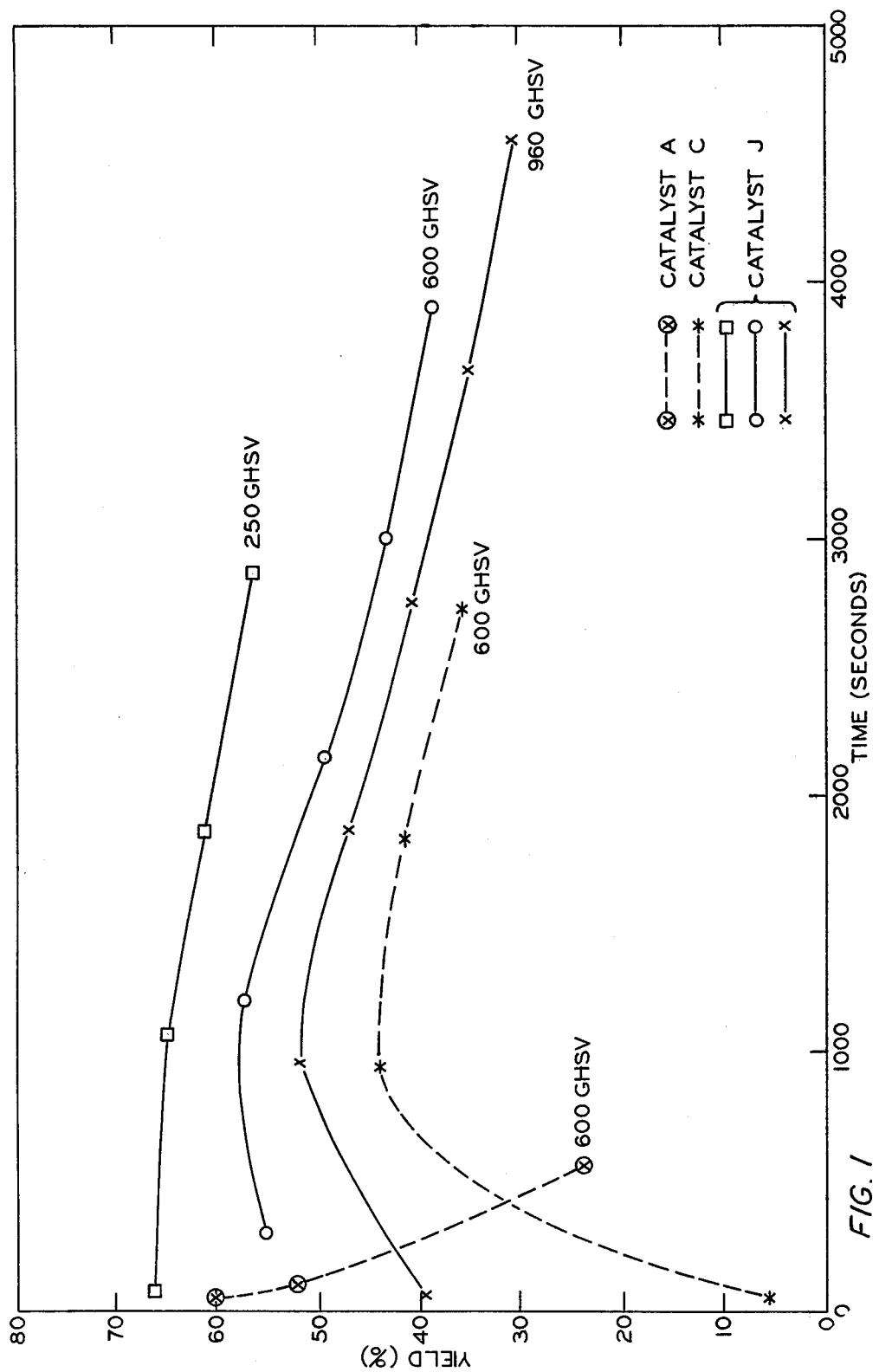

United States Patent [19]

Aldag, Jr.

[11] Patent Number: 4,463,213

[45] Date of Patent: Jul. 31, 1984

[54] DEHYDROGENATION OF ORGANIC COMPOUNDS WITH A ZINC TITANATE HYDROGEL

[75] Inventor: Arthur W. Aldag, Jr., Bartlesville, Okla.

[73] Assignee: Phillips Petroleum Company, Bartlesville, Okla.

[21] Appl. No.: 468,019

[22] Filed: Feb. 18, 1983

[51] Int. Cl.$^3$ .............................................. C07C 5/327
[52] U.S. Cl. .................................. 585/629; 585/661; 585/616
[58] Field of Search ...................... 585/629, 661, 616

[56] References Cited

U.S. PATENT DOCUMENTS

| 2,274,634 | 3/1942 | Heard | 208/135 |
| 2,900,349 | 8/1959 | Schwartz | 252/317 |
| 2,932,673 | 4/1960 | Melik | 585/629 |
| 3,277,207 | 10/1966 | Bajars | 585/629 |
| 4,144,277 | 3/1979 | Walker et al. | 585/433 |
| 4,176,140 | 11/1979 | Bertus et al. | 585/629 |
| 4,327,238 | 4/1982 | Eastman | 585/663 |
| 4,368,344 | 1/1983 | Kolts | 585/661 |

Primary Examiner—Delbert E. Gantz
Assistant Examiner—Cynthia A. Prezlock

[57] ABSTRACT

The catalytic dehydrogenation of at least one dehydrogenatable organic compound which has at least one

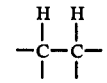

grouping is carried out in the presence of a zinc titanate hydrogel. The selectivity of the zinc titanate hydrogel may be improved by adding a promoter selected from the group consisting of lithium, sodium, potassium, rubidium and cesium.

18 Claims, 1 Drawing Figure

DEHYDROGENATION OF ORGANIC COMPOUNDS WITH A ZINC TITANATE HYDROGEL

This invention relates to an improved catalytic process for the dehydrogenation of organic compounds and a catalyst therefor.

Dehydrogenation processes for the conversion of organic compounds to compounds having a higher degree of unsaturation are well known. U.S. Pat. No. 4,144,277 teaches that zinc titanate is useful as a dehydrogenation catalyst in the dehydrogenation of organic compounds. U.S. Pat. Nos. 4,176,140 and 4,327,238 teach that various promoters can be used with the zinc titanate of U.S. Pat. No. 4,144,277.

While the zinc titanate catalyst of the above referenced patents is an excellent catalyst for dehydrogenation, the selectivity of the catalyst declines rapidly as a function of time. While the zinc titanate catalyst can be regenerated to restore its selectivity, it would be desirable to improve the zinc titanate catalyst in such a manner that selectivity does not decline as rapidly as a function of time and thus longer reaction periods can be used before regeneration is necessary. It is thus an object of this invention to decrease the rate at which the selectivity of the zinc titanate catalyst of the above referenced patents declines as a function of time and thus provide an improved process for the dehydrogenation of organic compounds where longer reaction times are desired.

In accordance with the present invention, a zinc titanate catalyst such as that taught by the above referenced patents is mixed with a hydrosol of a suitable acidic material. A suitable base is than added to the resulting mixture to form a hydrogel. The hydrogel is dried slowly and calcined to form what will be referred to as a zinc titanate hydrogel. A promoter selected from the group consisting of lithium, sodium, potassium, rubidium and cesium may then be added to the zinc titanate hydrogel to improve the performance of the zinc titanate hydrogel.

Once the zinc titanate hydrogel (either promoted or unpromoted) has been prepared, the zinc titanate hydrogel is utilized as a catalyst in a dehydrogenation process in which organic compounds are dehydrogenated in the presence of the catalyst to produce organic compounds having a higher degree of unsaturation.

The dehydrogenation process is preferably carried out in cycles consisting of a reaction period and a regeneration period for the catalyst. The reaction period comprises contacting a dehydrogenatable organic compound with the catalyst under suitable dehydrogenation conditions in the substantial absence of free oxygen to convert the dehydrogenatable organic compounds to compounds having a higher degree of unsaturation. After the reaction period, a free oxygen containing gas is passed in contact with the catalyst to regenerate the catalyst by burning off carbonaceous materials which may have been formed on the catalyst.

The use of the zinc titanate hydrogel results in a decrease in the rate at which the selectivity of the zinc titanate catalyst of the above referenced patents declines as a function of time. This enables the reaction period for the dehydrogenation process to be increased since regeneration is not necessary as often. Also, the use of the promoter improves the selectivity of the zinc titanate hydrogel especially early in the reaction period.

Other objects and advantages of the invention will be apparent from the foregoing brief description of the invention and the appended claims as well as the detailed description of the invention which follows.

The drawing is briefly described as follows:

FIG. 1 is a plot of the data from Example 2 which indicate the improvement provided by the present invention for a long reaction period.

The organic feedstocks which can be dehydrogenated in accordance with the present invention are dehydrogenatable organic compounds having from 2 to 12 carbon atoms per molecule and characterized by having at least one

grouping, i.e., adjacent carbon atoms, each having at least one hydrogen atom. Suitable compounds includes paraffins, olefins, cycloaliphatics and alkyl aromatic compounds having from 2 to 12 carbon atoms per molecule. Particularly suitable are paraffins having from 2 to 5 carbon atoms per molecule and monoolefins having from 4 to 5 carbon atoms per molecule, branched or unbranched. Some examples of suitable hydrocarbon feedstocks are ethane, propane, butane, isobutane, pentane, isopentane, hexane, 2-methylhexane, n-octane, n-dodecane, 1-butene, 2-butene, 2-methyl-1-butene, 2-methyl-2-butene, 2-hexene, 1-octene, 3-methyl-4-nonene, 1-dodecene, cyclohexane, and the like and mixtures of any two or more thereof. Particularly appropriate is the conversion of ethane to ethylene, propane to propylene, butanes to butenes and butadiene, butenes to butadiene, and isopentane to isoamylenes and isoprene.

The dehydrogenation catalyst employed in the process of the present invention is zinc titanate in a hydrogel of a suitable acidic material. In general, the catalyst composition is prepared by first preparing zinc titanate which is then reduced to a small size. The resulting material is mixed with a hydrosol of a suitable acidic material. A suitable base is then added to the mixture to form a hydrogel. The resulting hydrogel is dried slowly and calcined to form the zinc titanate hydrogel catalyst of the present invention. A promoter selected from the group comprising lithium, sodium, potassium, rubidium and cesium may be added to the zinc titanate hydrogel as will be more fully described hereinafter.

The zinc titanate portion of the catalyst composition may be prepared by intimately mixing suitable portions of zinc oxide and titanium dioxide, preferably in a liquid such as water, and calcining the mixture in the presence of free oxygen at a temperature in the range of about 650° C. to about 1050° C., preferably in the range of about 675° C. to about 975° C., to form zinc titanate. A calcining temperature in the range of about 800° C. to about 850° C. is most preferred because the surface area of the zinc titanate is maximized in this temperature range, thus producing a more active zinc titanate. The titanium dioxide used in preparing the zinc titanate preferably has extremely fine particle size to promote intimate mixing of the zinc oxide and titanium dioxide. This produces a rapid reaction of the zinc oxide and titanium dioxide which results in a more active zinc titanate. Preferably the titanium dioxide has an average particle size of less than 1000 millimicrons and more preferably less than 30 millimicrons. Flame hydrolyzed titanium dioxide has extremely small particle size and is particularly preferred in preparing the zinc titanate. The atomic ratio of zinc to titanium can be any suitable ratio. The atomic ratio of zinc to titanium will generally lie in the range of about 1:1 to about 3:1 and will preferably lie in the range of about 1.7:1 to about 2.1:1 because the activity of the zinc titanate is greatest for atomic ratios of zinc to titanium in this range. The term "zinc titanate" is used regardless of the atomic ratio of zinc to titanium.

The zinc titanate portion of the catalyst composition may also be prepared by coprecipitation from aqueous solutions of a zinc compound and a titanium compound. The aqueous solutions are mixed together and the hydroxides are precipitated by the addition of ammonium hydroxide. The precipitate is then washed, dried and calcined, as described in the preceding paragraph, to form zinc titanate. This method of preparation is less preferred than the mixing method because the zinc titanate prepared by the coprecipitation method is softer than the zinc titanate prepared by the mixing method.

The reuslting zinc titanate is reduced to a suitable size for mixing with a hydrosol of an acidic material by any suitable method such as treatment in an ultrasonic disrupter. The zinc titanate may be reduced to any suitable size with a particle size in the range of about 1 to about 5 microns being preferred.

The resulting zinc titanate having a fine particle size is mixed with a hydrosol of a suitable acidic carrier. Any suitable acidic carried such as an alumina, a silica-alumina or a zeolite material may be utilized. An alumina is preferred because it forms a well dispersed hydrosol phase. Alumina hydrate is particularly preferred because a hydrosol of alumina hydrate is readily converted to a hydrogel and then to the oxide phase after calcination.

After the zinc titanate has been thoroughly mixed into the hydrosol, a suitable base is added to convert the hydrosol to a hydrogel. Any suitable base such as alkali metal hydroxides, ammonium hydroxide, or urea may be utilized. Ammonium hydroxide is the preferred base because it does not have any metallic component that would remain in the hydrogel.

The resulting hydrogel is dried slowly so that water will not be removed so rapidly that the hydrogel structure will collapse which would result in excessive loss of pore volume and surface area of the finished zinc titanate hydrogel. Any suitable drying time can be utilized which does not result in too rapid removal of water. Preferably, the drying time is in the range of about 8 hours to about 24 hours.

Any suitable temperature can be utilized for the drying of the zinc titanate hydrogel but again the temperature should be such that too rapid removal of water does not result. The temperature is preferably in the range of about 35° C. to about 150° C. The most preferred drying condition is to start the drying process at about 80° C. and increase the temperature slowly to about 120° C. during the drying time.

After the zinc titanate hydrogel has been dried, the zinc titanate hydrogel is calcined in the presence of free oxygen. Any suitable free oxygen-containing gas may be utilized with air being preferred because of its availability. Also, any suitable time and temperature for the calcining may be utilized with a preferred time being about two hours and a preferred temperature being in the range of about 480° C. to about 600° C. Although the dried zinc titanate hydrogel can be placed directly into a preheated furnace or kiln for calcining, it is preferable for the catalyst to attain its final temperature during a heating period of about two hours.

The finished catalyst composition can contain any suitable weight percent of zinc titanate. In general, the amount of zinc titanate in the finished catalyst composition will be in the range of from about 10 weight percent to about 50 weight percent based on the total weight of the catalyst composition and will more preferably be in the range of from about 20 weight percent to about 40 weight percent based on the weight of the total catalyst composition.

The unpromoted zinc titanate hydrogel exhibits very poor selectivity early in the reaction. However, the selectivity of the zinc titanate hydrogel does improve rapidly and once the selectivity does improve this selectivity is maintained for a much longer period of time than the zinc titanate catalyst of the referenced patents.

The initial performance of the zinc titanate hydrogel can be improved by incorporating a promoter selected from the group consisting of lithium, sodium, potassium, rubidium and cesium. Also, the selectivity of the zinc titanate hydrogel is improved by the addition of the promoter.

The promoter is preferably added to the zinc titanate hydrogel by impregnation after the zinc titanate hydrogel has been calcined. The promoter may be added by any suitable method. Preferably, compounds of the promoter are dissolved in a suitable solvent (usually water) and the resulting solution is poured onto the zinc titanate hydrogel. The solvent is evaporated and the catalyst is dried and calcined at a temperature suitable to convert the promoter to an oxide. This technique utilized is generally referred to as incipient wetness impregnation in which the volume of the solution used to add the promoter to the zinc titanate hydrogel is essentially equal to the pore volume of the zinc titanate hydrogel.

The concentration of the promoter expressed as an element can be any suitable concentration. The concentration of the promoter expressed as an element will generally be in the range of about 0.3 to about 3 weight percent based on the weight of the zinc titanate hydrogel prior to treatment with the promoter and will preferably be in the range of about 0.5 to about 1.5 weight percent based on the weight of the zinc titanate hydrogel prior to treatment.

Any suitable temperature can be utilized to dry the impregnated zinc titanate hydrogel and to calcine the impregnated zinc titanate hydrogel. A suitable drying temperature is in the range of about 80 to about 150 C and a suitable calcining temperature is in the range of about 525 to about 650 C. Calcination again take place in the presence of free oxygen.

Any suitable compound of the promoter may be utilized to add the promoter to the zinc titanate hydrogel. Compounds which are directly convertible to the oxide are preferred. These compounds include hydroxides, carbonates, nitrates, acetates and salts of other carboxylic acids. Sulphur containing compounds such as sulfates can be used but are less preferred. Halogen containing compounds should be avoided. Of the promoters, lithium and sodium are the most preferred.

The dehydrogenation process of this invention can be carried out by means of any apparatus whereby there is achieved an alternate contact of the catalyst with the dehydrogenatable organic compound and thereafter of the catalyst with the oxygen-containing gaseous phase, the process being in no way limited to the use of a particular apparatus. The process of this invention can be carried out using a fixed catalyst bed, fluidized catalyst bed or moving catalyst bed. Presently preferred is a fixed catalyst bed.

In order to avoid any casual mixing of the organic compound and oxygen, provision is preferably made for terminating the flow of feed to the reactor and subsequently injecting an inert purging fluid such as nitrogen, carbon dioxide or steam. Any suitable purge time can be utilized. The purge duration will generally range from about 1 minute to about 10 minutes and will more preferably range from about 3 minutes to about 6 minutes. Any suitable flow rate of the purge fluid may be utilized. Presently preferred is a purge fluid flow rate in the range of about 800 GHSV to about 1200 GHSV.

Any suitable dehydrogenation reaction time may be used in the dehydrogenation process. The dehydrogenation reaction time will generally be in the range of about 1 second to about 24 hours and will preferably be in the range of about 30 minutes to about 8 hours.

Any suitable time for the regeneration of the dehydrogenation catalyst can be utilized. The time for the regeneration of the dehydrogenation catalyst will generally range from about 1 to about 10 times the reaction period. However, regeneration for a time longer than one hour will generally not be necessary for any reaction period.

Any suitable catalytic dehydrogenation temperature can be employed which provides the desired degree of catalytic activity in the dehydrogenation of the organic feedstock. The dehydrogenation temperature will generally be in the range of about 426° C. to about 705° C. and will more preferably be in the range of about 538° C. to about 677° C.

The catalytic dehydrogenation process can be carried out at any suitable pressure. The pressure of the dehydrogenation reaction will generally range from about 0.05 to about 250 psia.

Any suitable feed rate for the organic feedstock can be utilized. The organic feedstock feed rate will generally be in the range of about 50 to about 5,000 volumes of gaseous feedstock per volume of catalyst per hour and will preferably be in the range of about 100 to about 2500 volume of gaseous feedstock per volume of catalyst per hour.

A gaseous diluent, such as hydrogen or carbon dioxide, can also be utilized. If the gaseous diluent is utilized, the diluent to hydrocarbon molar ratio used will generally be in the range of about 0.1:1 to about 20:1.

The amount of free oxygen, from any source, supplied during the regeneration step will be an amount sufficient to remove substantially all carbonaceous materials from the catalyst. The regeneration step is conducted at the same temperature and pressure recited for the dehydrogenation step although somewhat higher temperatures can be used, if desired.

The operating cycle for the dehydrogenation and regeneration process will generally include the successive steps of:
(1) contacting a dehydrogenatable organic compound with the dehydrogenation catalyst;
(2) terminating the flow of the dehydrogenatable organic compound;
(3) optionally, purging the catalyst with an inert fluid;
(4) contacting the dehydrogenation catalyst with free oxygen;
(5) terminating the flow of the free oxygen; and
(6) optionally, purging the catalyst with an inert fluid before repeating step (1).

EXAMPLE 1

Zinc titanate was prepared by mixing Mallinckrodt powdered zinc oxide and Cab-O-Ti titanium dioxide (flame hydrolyzed) by slurrying in 150 mL of water in a blender for 5 minutes. The ratio of zinc oxide to titanium dioxide was such as to give an atomic ratio of zinc:titanium in the finished preparation of 1.8:1. The resulting slurry was dried in an oven at 105° C. and then calcined in air for three hours at 816° C. After cooling, the thus calcined material was crushed and screened, and a −16+40 mesh fraction was reserved for testing. A portion of the thus prepared zinc titanate was utilized as a control catalyst and is referred to hereinafter as Catalyst A.

The thus prepared powdered zinc titanate (54.1 grams) was slurried into 500 mL of water and treated with the transducer of an ultrasonic cell disrupter at high power for about 10 minutes to reduce the particle size of the zinc titanate to about 2–10 microns. The resulting slurry was combined with a suspension of 216 grams of alpha alumina monohydrate and about 900 mL of water. Sufficient nitric acid was added to the resulting mixture to lower the pH of the resulting mixture from about 7.6 to about 3.0 to produce the hydrosol. Ten mL of concentrated ammonium hydroxide was then added to the hydrosol to produce a hydrogel. The hydrogel was then dried in an oven for 18 hours at 82° C. and then the temperature was increased to 149° C. for 2 more hours. The thus dried hydrogel was then calcined in air in a furnace which was heated to 648° C. during 2 hours and then held at that temperature for 2 hours. The resulting zinc titanate hydrogel contained 20 weight percent zinc titanate based on the weight of the total hydrogel. The hydrogel was crushed and screened and a −16+40 mesh fraction was reserved for testing. This catalyst is referred to hereinafter as Catalyst B.

A second zinc titanate hydrogel was prepared in accordance with the above procedure except that the quantity of zinc titanate utilized was 108 grams and the quantity of alpha aluminum monohydrate utilized was 162 grams. The resulting zinc titanate hydrogel contained 40 weight percent zinc titanate based on the weight of the total hydrogel. This catalyst is referred to hereinafter as Catalyst C.

Catalysts B and C were impregnated with aqueous solutions of lithium or sodium as shown in Table I. The concentrations of the lithium and sodium were such as to give the concentrations in the finished catalyst composition stated in Table I. The stated concentrations were determined by chemical analysis.

TABLE I

| Catalyst | Catalyst Base | Conc. of Alkali Metal, wt. % | Form of Alkali |
|---|---|---|---|
| D | B | Na, 0.1 | NaOH |
| E | B | Na, 0.6 | NaOH |
| F | C | Na, 1.0 | NaOH |
| G | B | Na, 1.3 | NaOH |
| H | B | Li, 0.5 | LiOH |
| I | B | Li, 0.5 | LiOH |
| J | C | Li, 0.5 | LiNO$_3$ |
| K | C | Li, 1.4 | LiNO$_3$ |

Catalysts C–K were used in runs to dehydrogenate isobutane. The runs were made using −16+40 mesh catalyst in a quartz tubular reactor mounted vertically in a temperature controlled tube furnace. All runs were made at 625° C. and atmospheric pressure. The isobutane feed rate was 600 GHSV. Snap samples of reactor effluent were taken periodically and analyzed by GLC. Results of runs using these catalysts are presented in Table II.

TABLE II

| Catalyst | Time, sec. | i-C$_4$H$_{10}$ conv., % | Sel. to i-C$_4$H$_8$, % |
|---|---|---|---|
| C | 40 | 98.3 | 0 |
| C | 70 | 87.8 | 27.1 |
| C | 160 | 75.9 | 47.7 |
| D | 20 | 84.8 | 27.0 |
| E | 40 | 56.2 | 96.6 |
| E | 100 | 52.5 | 95.9 |
| E | 160 | 48.6 | 96.3 |
| F | 40 | 58.2 | 89.2 |
| F | 100 | 55.2 | 92.0 |
| G | 40 | 47.7 | 95.3 |
| G | 160 | 40.0 | 96.1 |
| H | 20 | 48.7 | 86.5 |
| H | 200 | 48.9 | 88.9 |
| I | 20 | 24.0 | 80.1 |
| I | 200 | 23.3 | 81.2 |
| J | 40 | 53.7 | 92.9 |
| J | 100 | 51.4 | 94.6 |
| K | 40 | 30.8 | 80.2 |
| K | 100 | 25.8 | 83.0 |

Catalyst C, although showing high initial activity, had very poor selectivity for dehydrogenation. Also Catalyst D with 0.1 weight percent Na had relatively poor selectivity. Catalysts E–K all exhibited much higher selectivity to produce isobutene from isobutane.

EXAMPLE 2

Runs were made for longer time periods using Catalysts A, C and J and the procedure of Example 1. All runs were again made at 625° C. and atmospheric pressure. The isobutane feed rate was as set forth in FIG. 1. Again, snap samples of reactor effluent at the times noted in FIG. 1 in which the results of the runs are presented.

Referring to FIG. 1, it can be seen that at the same isobutane feed rate, the promoted zinc titanate hydrogel exhibited a substantially improved yield (selectivity times conversion) especially in the early part of the reaction period. The initial yield for the zinc titanate which was not in the hydrogel form was high but this yield rapidly declined. It can thus be seen that substantially longer reaction periods can be maintained using the zinc titanate hydrogel and especially using the promoted zinc titanate hydrogel. The unpromoted zinc titanate hydrogel is not preferred because of its low initial activity but it could be utilized if the low initial activity was considered an adequate tradeoff for the fact that the unpromoted zinc titanate hydrogel will maintain activity for a longer period of time than the zinc titanate which is not in the hydrogel form.

Reasonable variation and modifications are possible within the scope of the disclosure and the appended claims to the invention.

That which is claimed is:

1. A process for the catalytic dehydrogenation of at least one dehydrogenatable organic compound which has at least one

group comprising the step of contacting said at least one dehydrogenatable organic compound under suitable dehydrogenation conditions in the substantial absence of free oxygen with a hydrogel of zinc titanate and a suitable acidic material selected from the group consisting of alumina, silica alumina and a zeolite, wherein the hydrogel of zinc titanate and a suitable acidic material allows a longer reaction period for the catalytic dehydrogenation process than the use of zinc titanate not in a hydrogel form.

2. A process in accordance with claim 1 wherein the concentration of zinc titanate in said hydrogel is in the range of about 10 to about 50 weight percent based on the weight of said hydrogel.

3. A process in accordance with claim 1 wherein the concentration of zinc titanate in said hydrogel is in the range of about 20 to about 40 weight percent based on the weight of said hydrogel.

4. A process in accordance with claim 1 wherein said suitable acidic material is alumina.

5. A process in accordance with claim 1 wherein said zinc titanate is prepared by calcining a mixture of zinc oxide and titanium dioxide in the presence of free oxygen at a temperature in the range of about 650° C. to about 1050° C.

6. A process in accordance with claim 1 wherein the atomic ratio of zinc to titanium in said hydrogel is in the range of about 1:1 to about 3:1.

7. A process in accordance with claim 1 wherein the atomic ratio of zinc to titanium in said hydrogel is in the range of about 1.7:1 to about 2.1:1.

8. A process in accordance with claim 1 wherein said hydrogel is formed by mixing powdered zinc titanate with a hydrosol of alumina hydrate to form a zinc titanate/alumina hydrosol, adding ammonium hydroxide to convert said hydrosol to a hydrogel and drying and calcining said hydrogel.

9. A process in accordance with claim 8 wherein said hydrogel is dried for a time in the range of about 8 to about 24 hours and at a temperature in the range of about 35° C. to about 150° C.

10. A process in accordance with claim 9 wherein the dried hydrogel is calcined in the presence of free oxygen at a temperature in the range of about 425° C. to about 650° C. for a time of about 2 hours.

11. A process in accordance with claim 1 wherein said hydrogel additionally comprises a promoter selected from the group consisting of lithium, sodium, potassium, rubidium and cesium.

12. A process in accordance with claim 11 wherein said promoter is lithium.

13. A process in accordance with claim 11 wherein said promoter is sodium.

14. A process in accordance with claim 11 wherein the concentration of said promoter expressed as an element is in the range of about 0.3 to about 3 weight percent based on the weight of said hydrogel.

15. A process in accordance with claim 11 wherein the concentration of said promoter expressed as an element is in the range of about 0.5 to about 1.5 weight percent based on the weight of said hydrogel.

16. A process in accordance with claim 1 wherein said dehydrogenatable organic compound is selected from the group consisting of paraffins having from 2 to 5 carbon atoms per molecule, monoolefins having from 4 to 5 carbon atoms per molecule, and mixtures of any two or more thereof.

17. A process in accordance with claim 1 wherein said suitable dehydrogenation conditions comprise a reaction period in the range of about 1 second to about 24 hours, a dehydrogenatable organic compound feed rate in the range of about 50 to about 5,000 volumes of dehydrogenatable organic compound per volume of said hydrogel per hour, a temperature in the range of about 426° C. to about 705° C., and a pressure in the range of about 0.05 psia to about 250 psia.

18. A process in accordance with claim 1 wherein said suitable dehydrogenation conditions comprise a reaction period in the range of about 30 minutes to about 8 hours, a dehydrogenatable organic compound feed rate in the range of about 100 to about 2500 volumes of dehydrogenatable organic compound per volume of said hydrogel per hour, a temperature in the range of about 538° C. to about 677° C., and a pressure in the range of about 0.05 psia to about 250 psia.

* * * * *